United States Patent
Leber et al.

(10) Patent No.: US 6,860,896 B2
(45) Date of Patent: Mar. 1, 2005

(54) THERAPEUTIC METHOD AND APPARATUS

(75) Inventors: Leland C. Leber, Fort Collins, CO (US); Robert Smith, Louisville, CO (US); Nathan R. Mortensen, Longmont, CO (US); Jeffrey T. Samson, 2555 Vassar Dr., Boulder, CO (US) 80305

(73) Assignee: Jeffrey T. Samson, Boulder, CO (US)

( * ) Notice: Subject to any disclaimer, the term of this patent is extended or adjusted under 35 U.S.C. 154(b) by 42 days.

(21) Appl. No.: 10/234,957

(22) Filed: Sep. 3, 2002

(65) Prior Publication Data

US 2004/0044384 A1 Mar. 4, 2004

(51) Int. Cl.[7] ............................................... A61N 1/00
(52) U.S. Cl. ............................ 607/1; 128/898; 607/88; 607/96
(58) Field of Search .................... 606/9; 607/88–91, 607/1; 128/898

(56) References Cited

U.S. PATENT DOCUMENTS

| | | | | | |
|---|---|---|---|---|---|
| 4,535,784 A | * | 8/1985 | Rohlicek et al. | ............ | 600/548 |
| 5,616,140 A | * | 4/1997 | Prescott | ........................ | 607/91 |
| 5,957,960 A | * | 9/1999 | Chen et al. | .................... | 607/92 |
| 6,096,066 A | * | 8/2000 | Chen et al. | .................... | 607/88 |
| 6,238,424 B1 | * | 5/2001 | Thiberg | ........................ | 607/88 |
| 6,290,713 B1 | * | 9/2001 | Russell | ........................ | 607/88 |
| 6,443,978 B1 | * | 9/2002 | Zharov | ........................ | 607/91 |
| 6,471,716 B1 | * | 10/2002 | Pecukonis | .................... | 607/89 |
| 6,494,900 B1 | * | 12/2002 | Salansky et al. | .............. | 607/89 |

FOREIGN PATENT DOCUMENTS

WO      WO01/68172 A1  *  9/2004  .......... A61M/21/00

* cited by examiner

*Primary Examiner*—Lee Cohen
*Assistant Examiner*—Henry M Johnson, III
(74) *Attorney, Agent, or Firm*—Patent Law Offices of Rick Martin, P.C.

(57) ABSTRACT

An energy therapy device is provided that utilizes an array of energy-emitting elements to stimulate Qi energy flow along acupuncture meridians. Energy-emitting elements are activated and deactivated sequentially to produce an energy wave. The energy wave is brought into contact with, or in close proximity to, anatomical sites on a patient's body that have underlying acupuncture meridians. The energy wave produced by the energy therapy device stimulates the flow of Qi energy resulting in a number of therapeutic benefits including pain relief, and reduction of inflammation.

9 Claims, 12 Drawing Sheets

THERAPEUTIC METHOD AND APPARATUS

BACKGROUND OF THE INVENTION

From the earliest recorded history of mankind, men have suffered from all manner of disease and injury. Whether it is found on the paintings and petroglyphs of early cave dwellers and cliff dwellers or in the 4700-year-old Huang Di Nei Jing (Yellow Emperor's Classic of Internal Medicine), there is a long history of Man's attempt to treat diseases and injuries. Most of this early medicine consisted of herbal remedies and, in the case of the ancient Chinese, acupuncture. The basis of modern western medicine has been formed in a large part from what was learned from the ancient Native Americans, Asians, Indians and Europeans. A large percentage of effort in medical research is spent on developing a scientific understanding of how some of these early remedies work.

Probably the most effective and yet least understood medical practice is acupuncture. Acupuncture dates back more than 5000 years. Shen Nung developed the theory and early practice of acupuncture. Shen Nung developed several theories on the function of the body, including the first concepts of circulation, pulse and the heart. He also developed the theory of an energy force flowing through the body along meridian lines. His term for this energy force was Qi (pronounced chee). Shen Nung theorized that Qi affects all aspects of a person, including emotional, spiritual and physical health. A person's health is affected by the flow of Qi in the body along with the universal forces of yin and yang. To maintain good health, it is necessary to maintain a balance. Shen Nung's meridian lines are divided among yin meridians and yang meridians. In general yin meridians flow up (from the earth) along the inside of the legs and arms while yang meridians flow down (from the sky/sun) along the outside of the arms, back and legs. Normally Qi energy constantly flows up and down along the meridian lines. When something happens to interrupt or block the flow of Qi energy, a disease state occurs.

Acupuncture meridians can best be characterized as 'channels', or "vessels" through which Qi energy flows and are sometimes associated with a clear, colorless liquid that flows within them (Thie, J. F., "A New Approach for Restoring our Natural Energies"; 1979.). Meridians and acupuncture points have also been characterized by lines and points of low electrical resistance located in the epidermis. These areas have been associated with the presence of gap junctions. These intercellular junctions are the basis of intercellular communications (Jingyu, F., et al., *Am. J. of Acupuncture*, 18(2), 163–170, 1990) Other researchers have suggested that meridians comprise electrically polarized molecules, such as water clusters having a permanent electrical dipole moment (Lo, S. *Med. Hypotheses*, 58(1), 72–76, 2002).

The understanding of the properties and characteristics of Qi energy and the meridians in which it flows has been gained primarily from the collective experience of many generations of acupuncture practitioners. However, recent efforts to detect the meridians and measure energy flow have been reported in the literature (Lo, supra; Jingyu, et al., supra; Zong-xiang, Z., *Am. J. of Acupuncture*, 9(3), 203–216, 1981; Darras, J-C., et al., *Am. J. of Acupuncture*, 20(3), 245–256, 1992) all of which are incorporated herein in their entirety to the extent not inconsistent herewith). For example, Lo used infrared imaging to show the effect of acupuncture on relieving pain by stimulating an acupuncture point (on a meridian associated with the pain area) that is far from the area of pain (Lo, supra). Darras et al. have also studied meridians by injection of radioactive tracers into traditional acupuncture points and studying the migration of the tracer. Results indicate that the tracer migrates preferentially along pathways that coincide with meridians described by traditional Chinese medicine. These pathways are reported as distinct from lymphatic or vascular pathways as shown by control experiments in which tracer that is injected in a non-acupuncture site does not show such preferential migration (Darras et al., supra).

Acupuncture meridians are located below the surface of the skin and are interconnected deep within the body. As mentioned above, they are arranged in two groups, based upon direction of flow. Yin meridians are associated with solid organs of the body while Yang meridians are associated with hollow organs. The twelve commonly acknowledged major meridians are listed in Tables 1 and 2. Numerous references illustrate the position of the meridians (see, e.g. Thie, J. F., "A New Approach for Restoring our Natural Energies"; 1979.) Numerous 'minor' meridians also exist.

TABLE I

Yang Meridians

| | |
|---|---|
| Stomach | From the right eye through the right chest, right stomach, down the front of the right leg to the right foot toes |
| Small Intestine | From the left hand, down the outside of left arm to back of left shoulder and up left side of face to the left ear |
| Bladder | From the left eye up over the head, down the neck down the central and left of back down the left leg to the left foot and toes |
| Triple warmer | From the left hand, down the underside(elbow) of the left arm through the triceps area to the shoulder and up the left side of the neck to the left eye |
| Gall Bladder | From the left eye over the top of the head, down the back of the neck, down the left side of the torso, through the outside of the left leg and into the left foot. |
| Large Intestine | From the tip of the left index finger down the outside of the left arm through the left shoulder up the left side of the throat and into the nose |

TABLE II

Yin Meridians

| | |
|---|---|
| Spleen | From the left big toe up the front of the left leg, up the left front side of the torso to just below the left arm pit |
| Heart | From the left arm pit up the underneath side of the left arm to the tip of the small finger |
| Kidney | From the bottom of the left foot to the back of the left heel, up the back inside of the left leg, up the center of the front of the torso to just left of the sternum |
| Pericardium | From the right upper quadrant of the chest to the shoulder, up the under side of the right arm to the tip of the second finger on the right hand |
| Liver | From the tip of the big toe on the left foot, back along the inside of the left foot, up along the inside of the left leg up along the left front portion of the lower torso and to the left front torso midway up the torso |
| Lung | From a point on the left front portion of the chest, up to the left shoulder, up the inside of the left arm to the tip of the left thumb |

The meridians are believed to all be connected end to end with each other such that Qi energy can flow from one to the other and form a continuous loop. They are arranged in the following order: gall bladder connected to liver connected to lung connected to large intestine connected to stomach connected to spleen connected to heart connected to small intestine connected to bladder connected to kidney connected to pericardium connected to triple heater connected to gall bladder Several therapies have been developed based on the flow of Qi energy along the meridians. These therapies are used to treat a wide variety of health conditions, mostly dealing with pain and healing of wounds and other more chronic conditions. Acupuncture is the first and most common of these therapies. It consists of inserting and manipulating small sharp needles at points, or nodes (acupuncture points) along the meridians that are considered blocking points to the flow of Qi. The needles act to unblock these meridians, restore the flow of Qi and restore health. Similar therapies are practiced where other methods are used to unblock these acupuncture points. Acupressure applies pressure to blocking points to restore the flow of Qi. Similarly, electrical stimuli, magnetic stimuli and point light sources are applied to acupuncture points to unblock meridians and restore the flow of Qi energy.

In western medicine, acute or chronic pain associated with arthritis, injuries and other non-specific pain conditions is often treated by manipulating the flow of blood. Changing the temperature of tissue being treated most often does this. It is a commonly held belief that heating a part of the body can increase blood flow to that part of the body, and furthermore that increasing blood flow also increases the rate of healing. There are many products that work on this premise, including heating pads, hot water bottles, heat lamps and light therapy devices.

In western medicine today, pulsed monochromatic light of various wavelengths is used as a therapy for the treatment of various muscular and skeletal disorders, including pain, swelling and injuries. This therapy is in limited use by chiropractors, physical therapists, sports medicine specialists, holistic medicine practitioners and medical doctors. Although the mechanisms of action are not well understood, it is generally held that pulsed light therapy in the visible and infrared range is effective by a combination of tissue heating, which increases localized circulation, and by photobiological effects (U.S. Pat. No. 6,290,713 of Thomas A. Russell for "Flexible Illuminators for Phototherapy" issued Sep. 18, 2001; U.S. Pat. No. 6,187,029 of Shapiro et al. for "Photo-thermal Treatment Device" issued Feb. 13, 2001; U.S. Pat. No. 6,096,066 of Chen and Wiscombe for "Conformal Patch for Administering Light Therapy to Subcutaneous Tumors" issued Aug. 1, 2000; U.S. Pat. No. 5,616,140 of Prescott for "Method and Apparatus for Therapeutic Laser Treatment" issued Apr. 1, 1997; U.S. Pat. No. 5,913,883 of Alexander and Brighton for "Therapeutic Facial Mask" issued Jun. 22, 1999; U.S. Pat. No. 5,358,503 of Bertwell and Markham for "Photothermal Therapeutic Device and Method" issued Oct. 25, 1994; U.S. Pat. No. 4,761,047 of Mori for "Light Rays Radiation Cloth for Medical Treatment" issued Aug. 2, 1988; U.S. Pat. No. 5,989,283 of Wilkens for "Irradiation Device, Especially for the Cosmetic, Diagnostic, and Therapeutic Application of Light" issued Nov. 23, 1999; U.S. Pat. No. 5,447,528 of Gerardo for "Method of Treating Seasonal Affective Disorder" issued Sep. 5, 1995; U.S. Pat. No. 4,671,285 of Walker for "Treatment of Human Neurological Problems by Laser Photo Simulation" issued Jun. 9, 1987; U.S. Pat. No. 6,249,698 of Parris for "Infrared Radiation Therapy Device" issued Jun. 19, 2001; U.S. Pat. No. 5,549,660 of Mendes et al. for "Method of Treating Acne" issued Aug. 27, 1996; U.S. Pat. No. 5,259,380 of Mendes et al. for "Light Therapy System" issued Nov. 9, 1993; U.S. Pat. No. 4,930,504 of Diamantolpoulos et al. for "Device for Biostimulation of Tissue and Method for Treatment of Tissue" issued Jun. 5, 1990; U.S. Pat. No. 5,800,479 of Thiberg for "Device for Medical External Treatment by Means of Light" issued Sep. 1, 1998; U.S. Pat. No. 6,238,424 of Thiberg for "Device for External Treatment with Pulsating Light of High duty Cycle" issued May 29, 2001 ;U.S. Pat. No. 6,238,425 of Thiberg for "Device for External Medical Treatment with Monochromatic Light" issued May 29, 2001; PCT Publication Number WO 01/68172 of Pederson et al. for "Light Therapy Device" published Sep. 20, 2001).

Many of these devices comprise a plurality of light sources of varying wavelengths that may be affixed to a flexible substrate. Light sources in some of these devices may be pulsed at different rates and operate at different duty cycles (i.e. ratio of time on to time off) and may be arranged in geometrical patterns.

For example, U.S. Pat. No. 6,290,713 discloses a light therapy device having a plurality of light-generating sources on a flexible substrate that uses a controller for controlling selective illumination of the light sources, light intensity and therapy time. The device may be passively or actively cooled, and may have a diffusive, or reflective layer that maximizes the light contacting the covered surface of the patient.

U.S. Pat. No. 6,187,029 describes an ergonomically shaped photothermal treatment device for a number of different anatomical surface positions of the human body. The photo thermal device comprises a plurality of LEDs and resistors housed in a contoured case. The LEDs may be pulsed or fired in a sequence to reduce body adaptation to treatment. A number of possible biochemical and physiological effects are described as relating to the use of the photo-thermal device, including increased oxidative enzyme activities, increased RNA synthesis and enhanced protein synthesis, and increased serotonin production, among others.

U.S. Pat. No. 6,096,066 describes a flexible patch with a plurality of light sources spaced in an array for photodynamic therapy (PDT). A controller may independently control the activation (schedule) of different groups of light sources, as well as their intensity and timing.

U.S. Pat. No. 5,616,140 describes a battery-operated, flexible, conforming portable laser bandage having one or a plurality of lasers and hyper-red light-emitting diodes that may be worn by a patient for treatment of specific body areas. A number of configurations of the device are disclosed, including a glove, sock, wrist band, and clothing. The device may be programmed to initiate operation for particular treatment time periods.

U.S. Pat. No. 5,358,503 describes a light and thermal therapy device comprising a flexible, conforming pad having a plurality of juxtaposed light-emitting diodes, each held in contact with the skin, and resistors to heat each diode. According to the disclosure in U.S. Pat. No. 5,358,503, LEDs are positioned in the device to assure complete coverage of the treatment area. LEDs are arranged in a plurality of rows. Diodes in rows are connected in series with each other and the rows are additionally connected in parallel with other rows. A rheostat controls the light intensity of the diodes as well as the amount of heat generated by the resistors.

U.S. Pat. No. 4,930,504 describes a device comprising a plurality of monochromatic light sources, preferably of three different wavelengths, arranged such that radiation of at least two different wavelengths passes through a single point on a treatment area. This device can be configured in either a single beam probe, or a cluster probe having the light sources arranged in different geometric patterns and further comprises a power supply and a control unit for modulating pulse frequency and treatment time.

U.S. Pat. No. 6,249,698 describes the use of a plurality of energy transducers, including light sources, the output of which is modulated at audio or sub-audio frequencies. The transducers are regulated by a system to control their timing and sequence of operation.

In addition to the photothermal devices discussed above, a number of devices are designed to stimulate one or more acupuncture points. It is also generally believed that light therapy directed at specific acupuncture points is effective at unblocking energy flow in acupuncture meridians. There are several prior art devices which unblock meridians by use of pulsed or continuous light applied to the classic acupuncture points much like the use of needles, magnets or pressure is used at these points to unblock energy flow. (U.S. Pat. No. 6,238,425 of Thiberg for "Device for External Medical Treatment with Monochromatic Light" issued May 29, 2001; U.S. Pat. No. 5,643,173 of Welles for "Method and Apparatus for Stress Relief" issued Jul. 1, 1997; U.S. Pat. No. 4,535,784 of Rohlicek et al. for "Apparatus for Stimulating Acupuncture Points by Light Radiation" issued Aug. 20, 1985; and U.S. Pat. No. 4,553,546 of Javelle for "Assembly for Regulating the Energy Circulating in the Meridians and Method of Use" issued Nov. 1985; and U.S. Pat. No. 6,221,095 of Van Zuylen et al. for "Method and Apparatus for Photon Therapy" issued Apr. 24, 2001.

U.S. Pat. No. 6,238,425 describes a device comprising a plurality of monochromatic light sources wherein one or more wavelengths of light are represented in the plurality. A drive including a selector is also provided for controlling treatment time and pulse frequency of the light sources. The light sources having different wavelengths may be separately controlled, allowing treatment in stages by different wavelength light. U.S. Pat. No. 6,238,425 also describes using the device to stimulate acupuncture points by choosing suitable wavelengths and pulse frequencies.

U.S. Pat. No. 6,221,095 describes a flexible, conforming device comprising a plurality of light sources for directing light to a treatment area and a control unit that may operate in conjunction with a personal computer or independently for portable use. The control unit may store a number of prescribed treatments and may control treatment type, time, etc. The light sources may operate in continuous wave, modulated, or pulsed modes and may be directed to acupuncture points.

U.S. Pat. Nos. 5,643,173; 4,535,784; and 4,553,546 all describe the therapeutic use of light directed at a specific acupuncture point. U.S. Pat. No. 5,643,173 describes a square wave generator for directing a square wave through a human body in combination with LEDs for directing light to pre-selected acupuncture points. U.S. Pat. No. 4,535,784 describes a single light-emitting diode for stimulating an acupuncture point combined with an electrode surface for locating the acupuncture point. U.S. Pat. No. 4,553,546 describes an apparatus for the application of pulsed infrared light to traditional acupuncture points, and further discloses the use of two such apparatuses to stimulate both an inductive acupuncture point and a directive acupuncture point to cause energy to flow in a particular direction.

It is known in the art that 'tracing' (e.g. with light touch) the acupuncture meridians, or parts of the acupuncture meridians, can stimulate energy flow along them (Thie, J. F., "A New Approach for Restoring our Natural Energies; 1979.) Such tracing is different from the stimulation of individual acupuncture points, or nodes, located along the meridians to unblock the flow of energy through the individual nodes. There is a need in the art for a device capable of tracing the meridians, or portions of the meridians to stimulate energy flow in them. The device and methods of the present invention satisfy such a need.

All publications referred to herein are incorporated by reference to the extent not inconsistent herewith.

SUMMARY OF THE INVENTION

This invention represents the marriage of eastern and western medical practices with a method and device embodied in an easy-to-use form. The benefit of heating tissue to enhance blood flow, reduce pain and encourage healing and the benefit of unblocking, redirecting and regulating the flow of Qi energy along acupuncture meridians are both provided with this invention. The device of this invention provides therapeutic benefits by warming tissue using pulsed visible and infrared light and by stimulating the flow of Qi energy in the acupuncture meridians by the application of a traveling wave of energy (e.g. light) in the direction of flow of Qi energy in the acupuncture meridians. Qi waves are stimulated in accordance with different patterns to treat specific conditions as is known in the art.

In its most general form, the light therapy device of this invention comprises a) a substrate;

b) a plurality of groups of energy-emitting elements attached to said substrate;

wherein, during operation, said substrate is positioned such that energy from said energy-emitting elements contacts a patient's body, or portions thereof, and said energy-emitting elements are positioned over at least a portion of an acupuncture meridian;

c) a drive circuit in electrical connection with said groups of energy-emitting elements; and d) a control unit in electrical connection with said drive circuit programmed to cause said drive circuit to pulse said energy-emitting elements on and off in a wave directed along said acupuncture meridian.

The substrate and attached energy-emitting elements may also be referred to, in combination, as a treatment pad. The treatment pad may also optionally include additional protective or structural layers.

As used herein, used with respect to energy-emitting elements, the term "group" refers to one or more energy-emitting elements. For example, a group may be a single energy-emitting element, a row of energy-emitting elements, multiple adjacent rows of energy-emitting elements, or some other type of cluster of energy-emitting elements.

Groups of energy-emitting elements may form an array. The term 'array' as used herein refers to an orderly arrangement of energy-emitting elements, e.g. a line, a series of columns and rows, a spiral, or other orderly arrangements.

In one embodiment of this invention, the energy-emitting elements are arranged in rows. Energy-emitting elements within a row may be electrically connected in series such that all energy-emitting elements in a row are activated at the same time. Parallel rows in a series may be separately activated from one another such that they may be activated sequentially. In a preferred embodiment, the therapy device is applied to a patient's body such that the wave created by activating the energy-emitting elements sequentially is aligned with one or more of the patient's acupuncture meridians, or a portion of one or more acupuncture meridians, to encourage the flow of Qi energy.

This invention also provides methods for the use of the energy therapy device disclosed.

BRIEF DESCRIPTION OF THE DRAWINGS

FIG. 9A depicts an ear and jaw pad. FIG. 9B depicts a face and nasal pad.

DETAILED DESCRIPTION OF THE INVENTION

Figure 1:
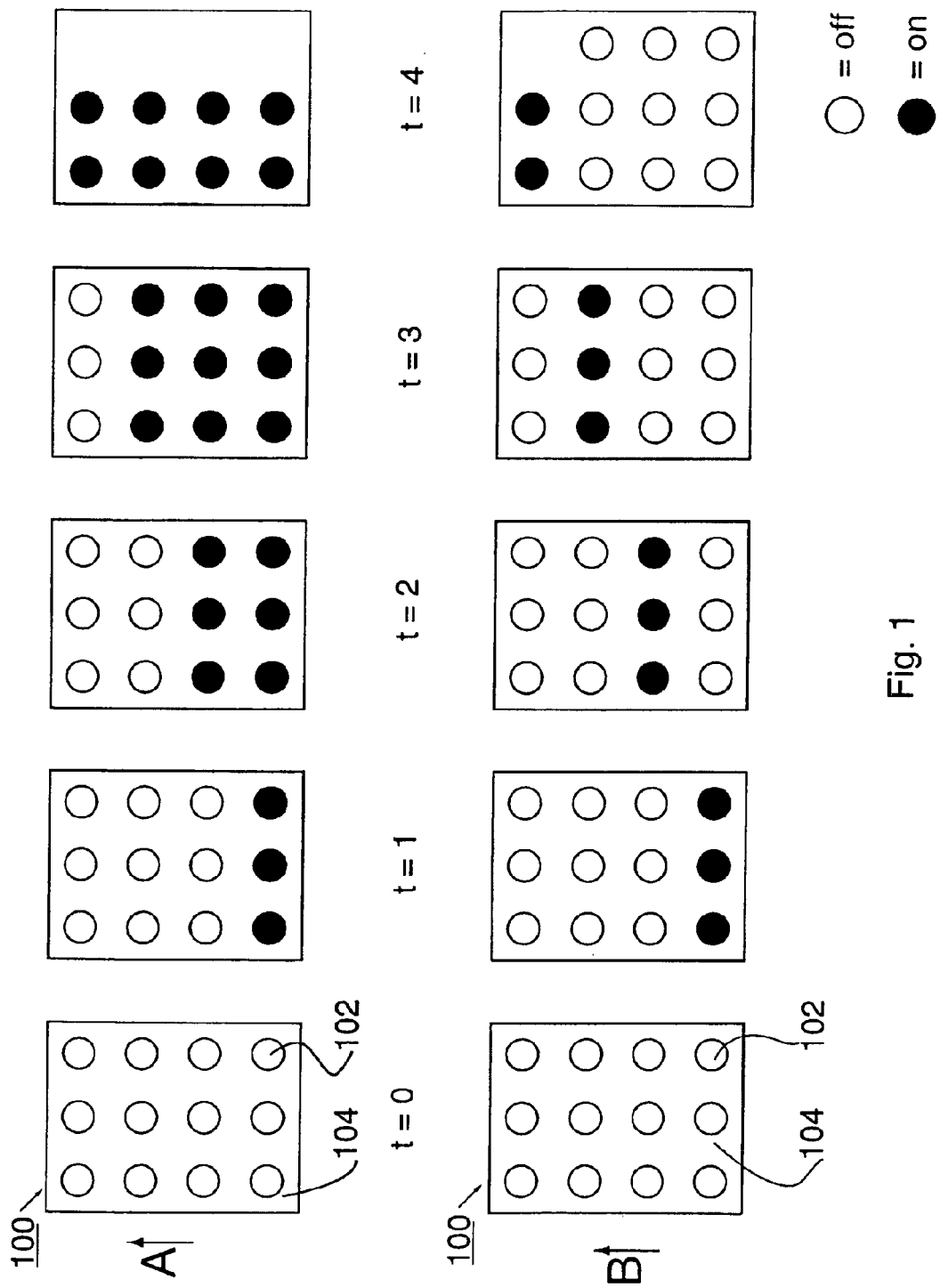
FIGS. 1A and 1B show two embodiments of light arrays which create an energy wave in a device of this invention.

This invention provides a therapy device having a plurality of energy-emitting elements mounted on a substrate in a defined spatial pattern, or array. The term "array" as used herein, refers to an arrangement of energy-emitting elements. The array may be a regular array, such as a line, a series of columns and rows, or a spiral, or a random array.

The energy-emitting elements may be any energy source. Energy-emitting elements must be able to be turned on (activated) and off (deactivated), and/or modulated between high and low intensities. Energy-emitting elements include all visible and infrared light sources (light-emitting elements), but also include other energy sources such as magnets, electromagnets, electrodes, thermal energy sources, acoustic wave sources, pressure sources, or X-ray sources. Thermal energy sources include electroresistive devices and infrared sources among others. Pressure sources include pneumatic, hydraulic and mechanical devices. Acoustic wave sources include those emitting in the 8–14 hz range.

In preferred embodiments of the device of this invention, the energy-emitting elements are light-emitting elements. Light sources include, for example, light-emitting diodes (LEDs), incandescent bulbs, lasers, halogen gas bulbs, and electroluminescent sources. Light sources may emit light of any wavelength within the visible and infrared, and ultraviolet ranges, and may also emit white light, broad spectrum light, monochromatic or polychromatic light. The light-emitting elements in an array may emit at a common wavelength or at different wavelengths. The wavelength for a given element may also be changed during operation, or between sessions, by means known in the art. The choice of light source type, as well as wavelength, is made by the practitioner based on the treatment area and the therapeutic effect desired. For example, numerous examples exist of the therapeutic application of color to treat a variety of medical conditions. See, for example, Liberman, J. et al., *Light Years Ahead: The Illustrated Guide to Full Spectrum and Colored Light in Mindbody Healing,* 1996; Corvo, J and Verner-Bonds, L., *Healing with Color Zone Therapy,* 1998; Andrews, T., *How to Heal with Color,* 2001; Russell, T. A., supra; Mendes, E., et al., U.S. Pat. No. 5,549,660.

In a preferred embodiment of this invention, light-emitting elements are infrared or visible LEDs. Preferably, the wavelength of the visible light LEDs is between 400 nm and 700 nm. More preferably, the wavelength of the visible light LEDs is between 600 nm and 660 nm. Most preferably, the wavelength of the visible light LEDs is 660 nm. Preferably, the wavelength of the infrared light LEDs is between 700 nm and 900 nm. More preferably, the wavelength of the infrared light LEDs is between 750 nm and 850 nm. Most preferably, the wavelength of the infrared light LEDs is 850 nm.

The substrate to which the energy-emitting elements are attached may be any flexible or rigid material including metals, polymers, cloth (synthetic and natural fibers), plastics, wood, fiberglass, rubber and the like. Preferred embodiments of this device utilize flexible substrates including flexible printed circuit boards as are known in the art. Preferably, the substrate is a flexible substrate that can be made to conform to anatomical sites on the patient's body. As used herein, the terms "conform" or "conforming" are used to describe a substrate that can be bent or formed to the approximate shape of the anatomical site being treated and that, when secured to the treatment area, allows all of the energy-emitting elements to be either approximately equidistant from the patient's skin or to touch the skin.

Figure 7:
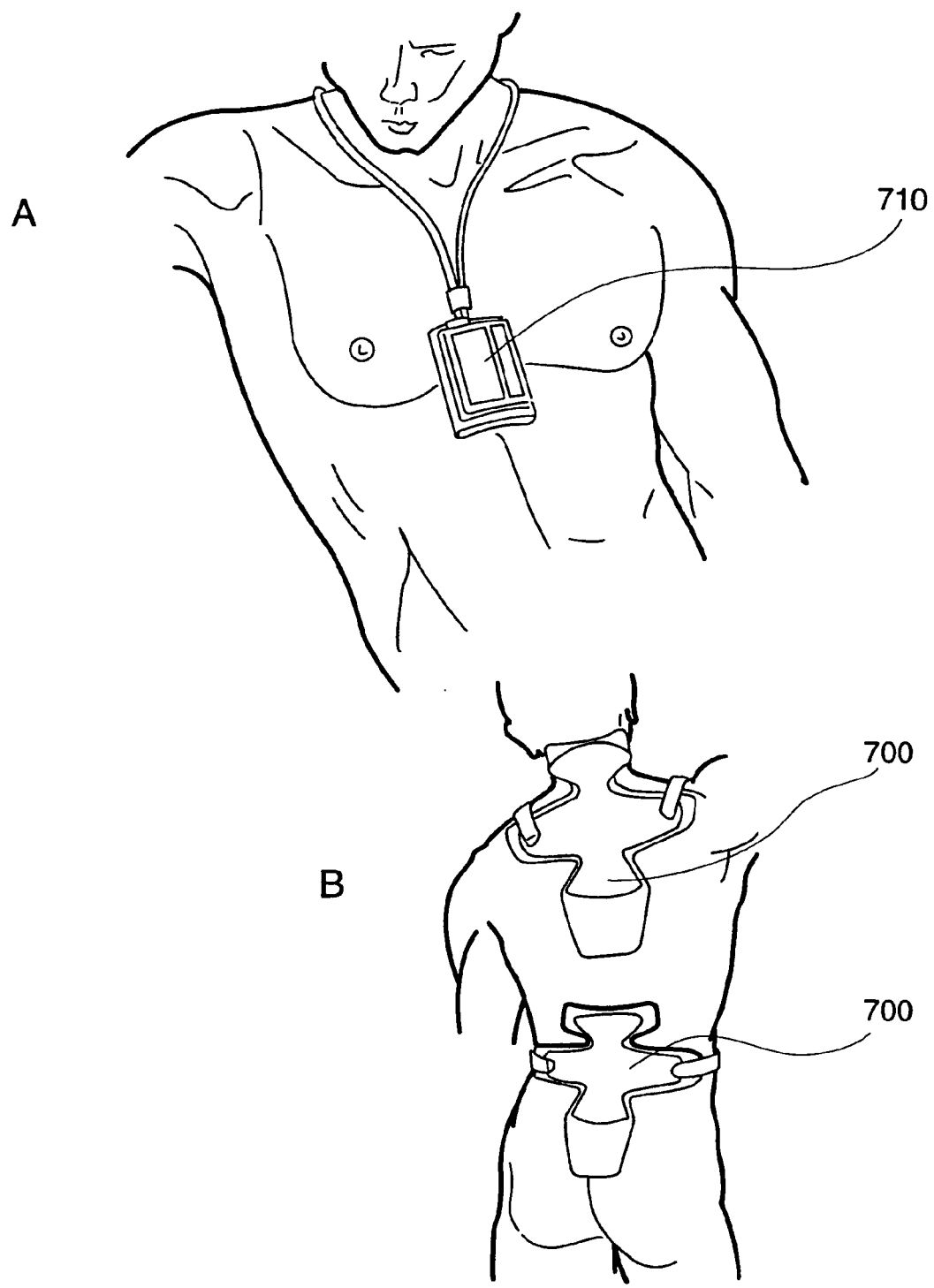
FIG. 7A shows an embodiment of this invention for use in treating areas of the upper and lower back, or other flat anatomical sites.
FIG. 7B shows one embodiment of how the control unit of the device of this invention can be worn by the user.
Figure 8:
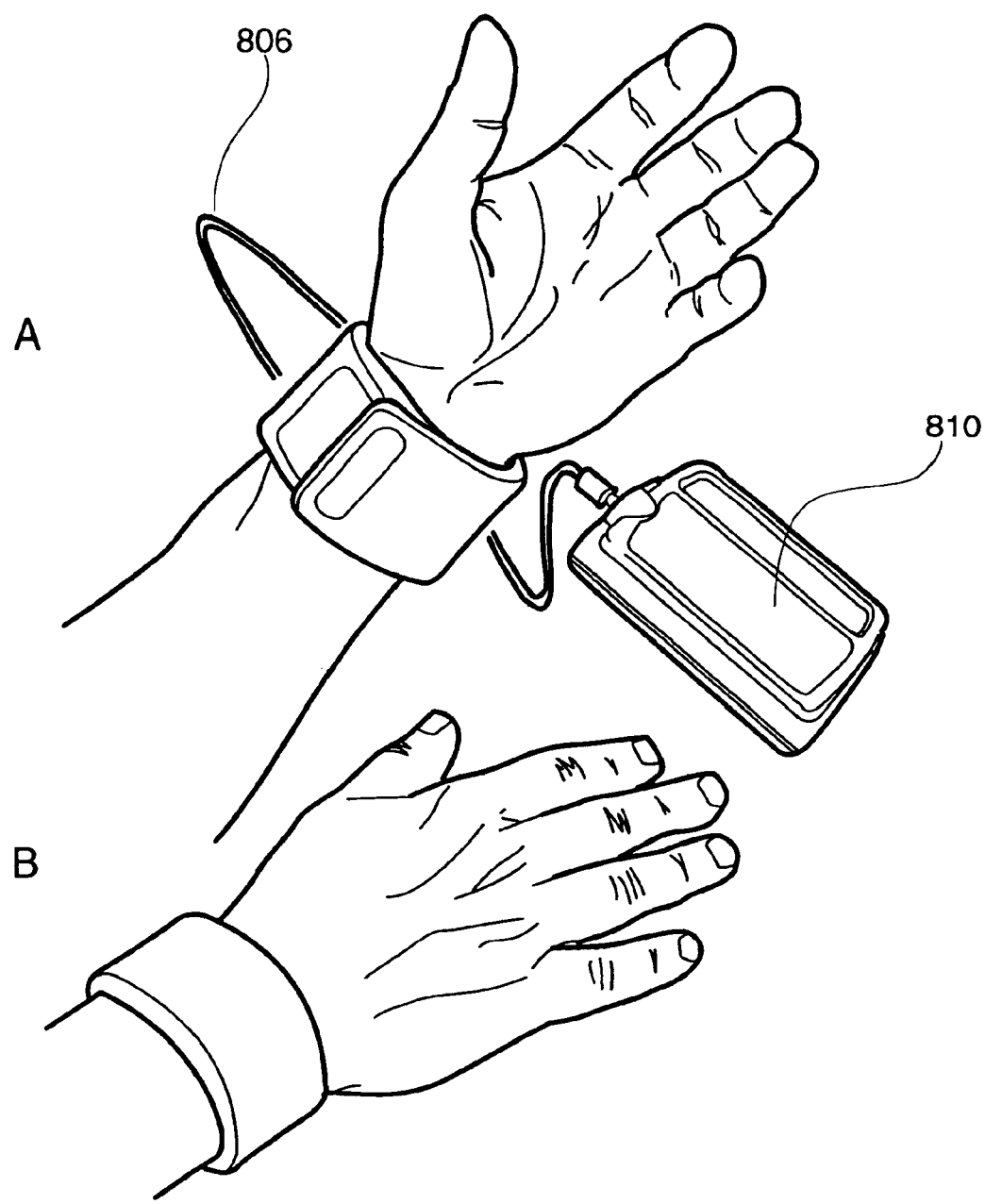
FIGS. 8A and 8B show a wrap-around embodiment of the device of this invention suitable for application to round anatomical sites such as limbs.
Figure 9:
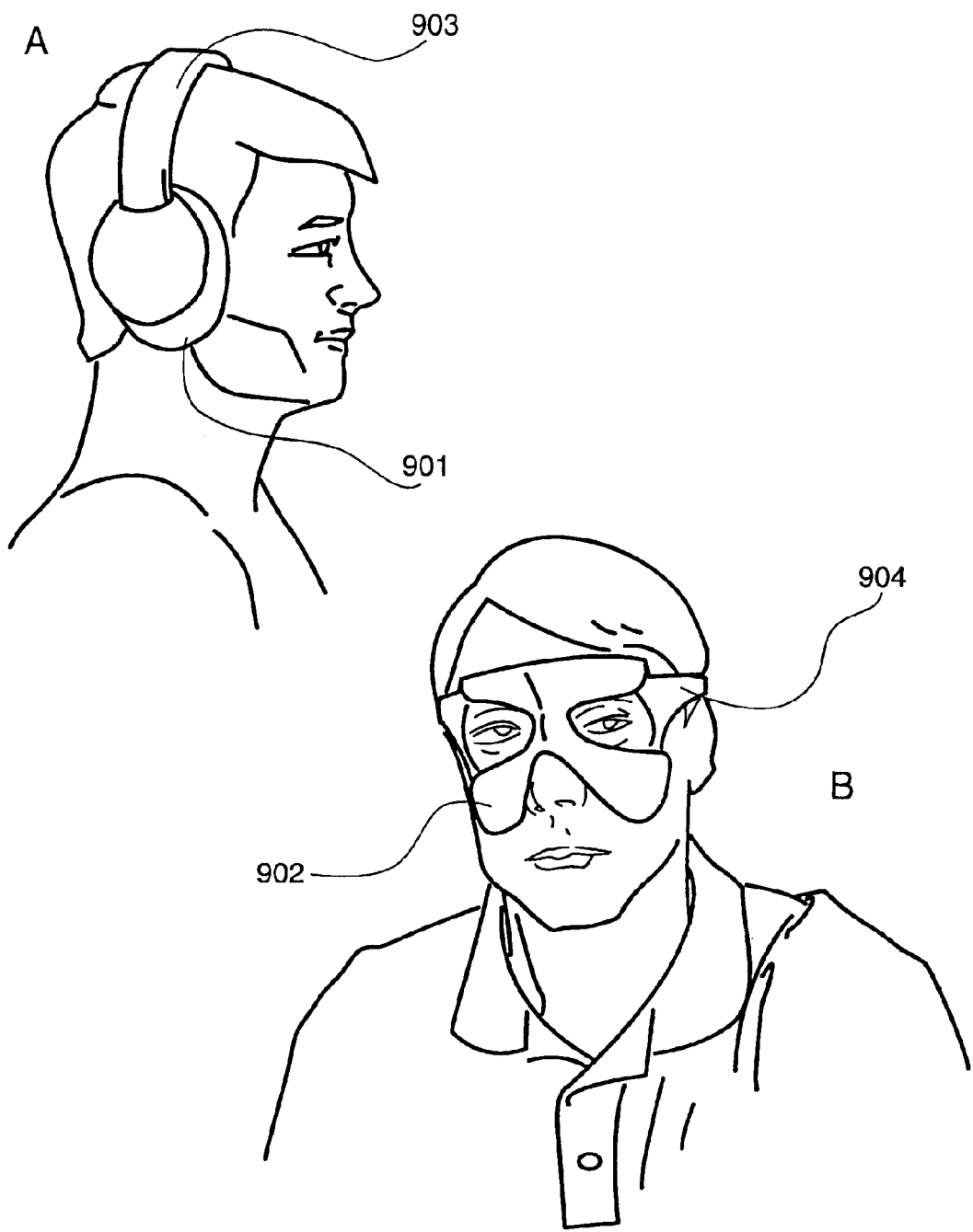
FIGS. 9A and 9B show examples of the device of this invention designed for specific anatomical sites.

The device may be applied, or secured to an anatomical site of interest using any number of attachment means known in the art. The device may be fitted with Velcro®, snaps, buttons, straps for tying, elastic straps, and the like to facilitate wrapping the device around a limb, for example, as in FIGS. 8A and 8B, or draping and securing the device across a relatively flat area as in FIGS. 7A and 7B. Alternatively, the device may be held in place during treatment by the patient or practitioner, or may be mounted on an adjustable stand.

Anatomical sites that are treatable with this device include, but are not limited to, the elbow, knee, shoulder, ankle, wrist, neck, upper spine, lower spine, foot hand, hip, ears, sinuses, jaw, stomach, chest, pelvic area, and portions of the same. In addition, tissues and organs underlying these anatomical sites may also be treated with the device of this invention. In some instances, treatment of anatomical sites, or therapy directed at relieving pain in a particular area of the body, may include application of the device at that site, or at another anatomical site. For example, treatment of injury or pain at the deltoid muscle may benefit from stimulation of Qi energy flow along the lung meridian (Thie, J. F., supra).

Energy-emitting elements are connected to each other by point-to-point wiring, printed circuit technology, die cut conductors laminated to flexible substrates, or other methods of electrical connection known in the art such that the energy-emitting elements can be activated individually or in groups, in sequences that create an energy wave along the device. For example, FIGS. 1A and 1B show two embodiments of energy-emitting element arrays that create an energy wave pattern in a device of this invention by the sequential activation and deactivation of rows of energy-emitting elements. In these examples, the energy-emitting elements are LEDs.

In FIG. 1A at time t=0, no LEDs 102 are on, or activated. At t=1, a first group of LEDs is turned on. At t=2, the first group remains on, and a second group of LEDs is also activated. This continues until t=4 when all groups are activated. An alternative energy wave pattern is shown in FIG. 1B in which only one group of LEDs is on at any given time. At time t=1, a first group of LEDs is turned on. At t=2, group 1 is turned off, and group 2 is turned on. In this manner, an energy wave is created by the device of this invention that travels, in these examples, from the bottom to the top of the substrate (104) of the treatment pad (100). Numerous other activation and deactivation sequences are readily apparent to one of ordinary skill in the art, and will result in other energy wave patterns. A wave cycle is defined as the completion of one pass of, for example, the activation of all groups in the array. The wave rate (number of cycles per unit of time) may be variable and is dependent on the type of wave pattern chosen, the size of the array, and the blink rate of the energy-emitting elements, among other factors. Preferably, the wave rate is greater than or equal to the rate of Qi flow within the meridians, which is approximately 3–10 cm/min (Darras, J-C, et al., supra).

In practice, the therapy pad of the device of this invention is applied, or secured, to an anatomical site on a patient's body such that the output of the energy-emitting elements is directed towards the patient's skin such that the energy wave created by the device is aligned to travel in the direction of one or more acupuncture meridians, or portions of one or more acupuncture meridians. This causes a corresponding wave, or flow of Qi energy along the underlying meridians.

Those of ordinary skill in the art will recognize that energy-emitting elements may be configured in many patterns to form arrays other than rows. In addition, the direction of the energy wave created by the activation and deactivation of the energy-emitting elements of the device relative to an anatomical site on a patient's body, can be changed, either electronically or by changing the application orientation of the treatment pad. For example, the energy-emitting elements may be activated such that the wave travels in either direction (e.g. bottom to top, or top to bottom). This is particularly useful for stimulating different meridians, for example on the same limb, that may flow in opposite directions. Similarly, multiple arrays may be employed on one treatment pad such that the energy wave of one array travels in one direction and the energy waves of other arrays travel in other directions. The arrays may be used individually or two or more of the arrays may be used simultaneously. Other patterns that create such an energy wave by activation and deactivation of energy-emitting elements will be readily apparent in the art.

In addition to encouraging Qi energy flow in the meridians, the intensity and quantity of light-emitting elements in this invention are optionally sufficient to cause deep tissue heating through the absorption of light energy, resulting in the dilation of blood capillaries, which leads to increased blood flow and a consequent improvement in healing rate of wounds and strains.

The treatment pad is optionally integrated into a support assembly that protects the circuit from moisture or other damaging agents and provides a comfortable and effective means for attaching the device to different anatomical sites on the patient's body. The support assembly may comprise a single layer, a pocket or pouch, or multiple layers, also referred to as 'protective layers'. Protective layers may be used to provide space between the energy-emitting elements and the patient's skin, cushioning for wearing comfort, and/or structural support. The protective layers may be smooth, or may be textured to include channels and the like. Channels may be used to allow air to flow between the treatment pad and the patient's skin. Optionally, protective layers may incorporate heating and cooling means to supplement the therapeutic effects of the energy-emitting element array. Heating means include, among others, electrical resistance elements, infrared LEDs, infrared incandescent elements, and Peltier heating elements. Cooling means include, among others, Peltier cooling elements. Protective layer material(s) may be flexible or rigid and for layers that lie between the energy-emitting elements and the patient's body, the material is transparent, i.e. transmissive, or partially transparent to the output of the energy source utilized in the device. For example, where light-emitting elements are used as the energy source, the support assembly material is transparent or semitransparent at the wavelength(s) of the light-emitting elements. Optionally, only the parts of the protective layer material that are aligned with the energy-emitting elements may be transparent. The support assembly may encase the device, or it may be attached to the device only on the side that is in contact with the patient's skin. The support assembly material may be disposable or re-usable, and if re-usable is preferably made of material that can be sterilized. Such materials are known in the art.

The array of energy-emitting elementsis connected to a control unit via a drive circuit. The drive circuit is comprised of one or more devices capable of interrupting the flow of energy from the power source to the energy-emitting elements, under the direction of the control unit. In the embodiment of this invention where the power source is an electrical power source, the internipion devices are, for example, transistors and/or relays. The control unit provides power to the energy-emitting elements through the drive circuit to activate the energy-emitting elements in a prescribed pattern and allows the user or practitioner to select certain aspects of the spatial and temporal pattern of the energy-emitting elements such as blink rate (on/off rate) of individual energy-emitting elements or groups of energy-emitting elements, cycle duty (the ratio of 'on' to 'off'), timing of the energizing of energy-emitting elements relative to each other to create a wave of energy (as discussed above) of a desired rate, energy-emitting element intensity, direction of energy wave, and total treatment time. For example, in one embodiment of this invention, the energy-emitting elements are LEDs and the LEDs are turned on and off (blink) at a rate between 5 hertz and 80 hertz. In another embodiment, the user may select a mode that causes the blink rate of the LED's to cycle through the entire range from 5 to 80 hertz on a continuous basis. These and other parameters are selected by the practitioner or user based on the therapeutic benefit that is desired.

The control unit also includes a user interface to accept programming and control inputs and to display settings and other information to the user. Optionally, the control unit may interface with or be a personal computer (PC) for both programming and data collection by the PC.

Another embodiment of this invention allows for a 'split' in the intelligence of the device between a removable control unit and the treatment pad resulting in a preprogrammed portable treatment device. The device comprises a treatment pad into which is integrated a non-volatile memory module for storing programmed settings, and a drive circuit used to activate the energy-emitting elements. Nonvolatile memory is any type of memory that retains its content when the power is turned off. Such non-volatile memory modules are known in the art and include non-volatile random access memory (NVRAM); electrically eraseable, programmable read-only memory (EEPROM); and battery backed up random access memory (RAM). The non-volatile memory is programmed using a detachable control unit, or via a connection to a PC. The control unit or PC connection is removed from the pad once programming is complete. The patient may then operate the device via a simple on/off switch and/or by selecting one of several pre-programmed operation settings. In such an embodiment, a portable power supply, such as a battery, may be integrated into the treatment pad to supply power to the device.

Figure 2:
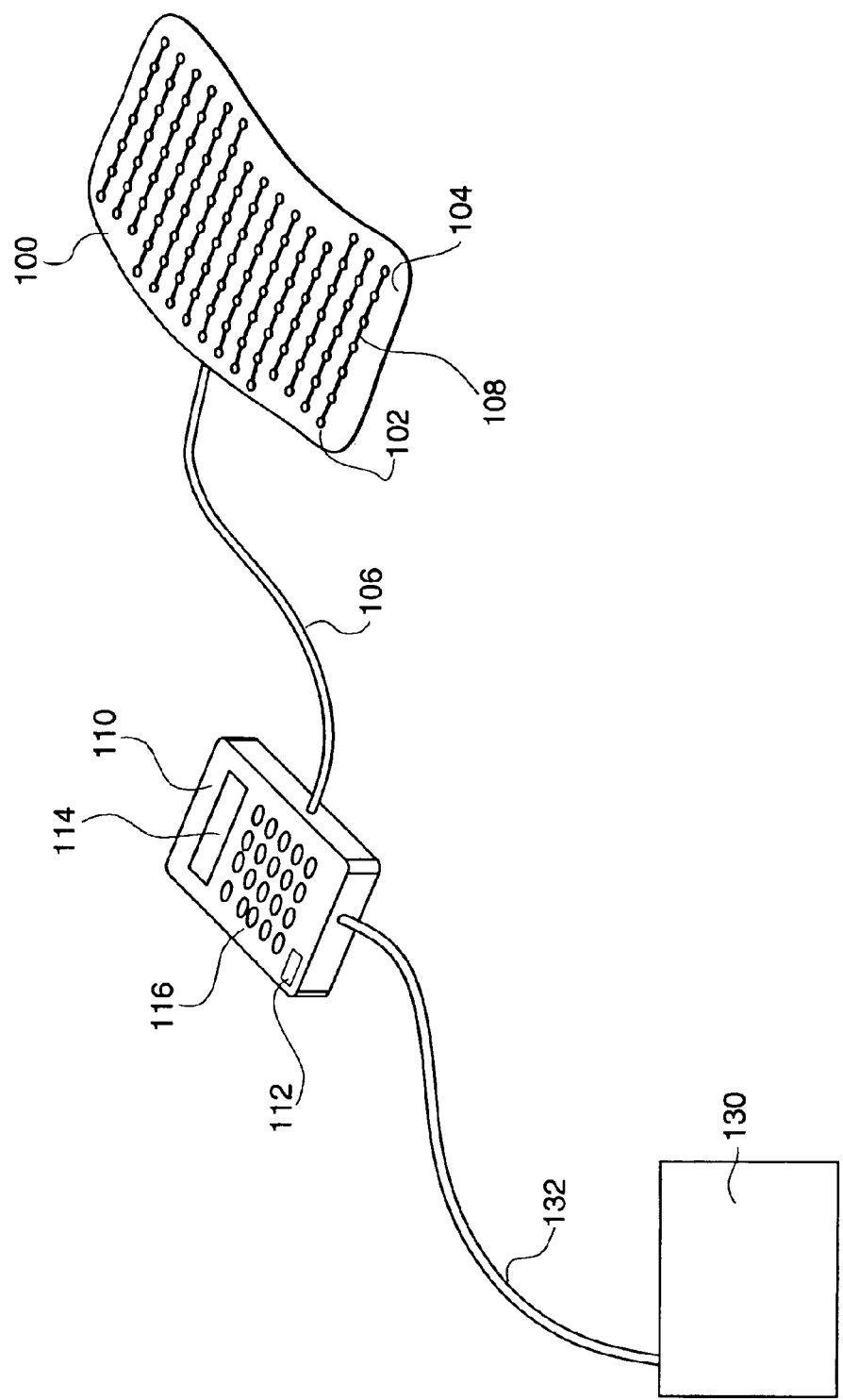
FIG. 2 shows one embodiment of the therapy device of this invention.
Figure 12:
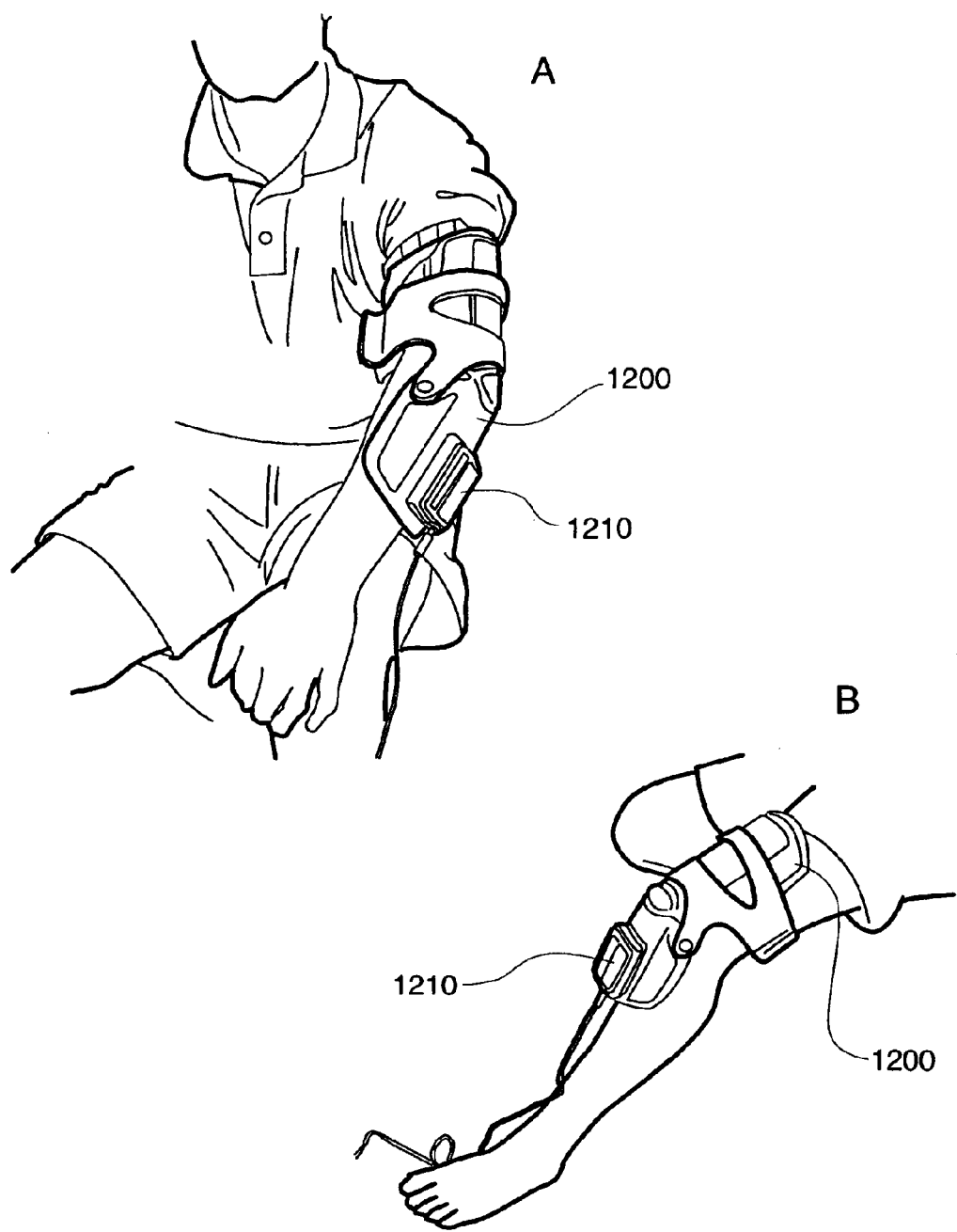
FIGS. 12A and 12B show one embodiment of this device designed to be applied to a flexible joint such as a knee or an elbow.

FIG. 2 shows one embodiment of the device of this invention. A plurality of energy-emitting elements 102 are arranged in an array of rows and columns on substrate 104 to form treatment pad 100. The energy-emitting elements are electrically connected to each other via electrical connections 108 and connected to control unit 110 via cable 106. Control unit 110 comprises a user input module 116 (e.g. a keypad), a feedback module 114 (e.g. an LCD screen) and optional computer interface 112. Power is supplied to the control unit and energy-emitting element array from power source 130 via power cable 132. Optionally, control unit 110 is mounted directly on to the device pad, as shown in FIGS. 12A and 12B.

Figure 3:
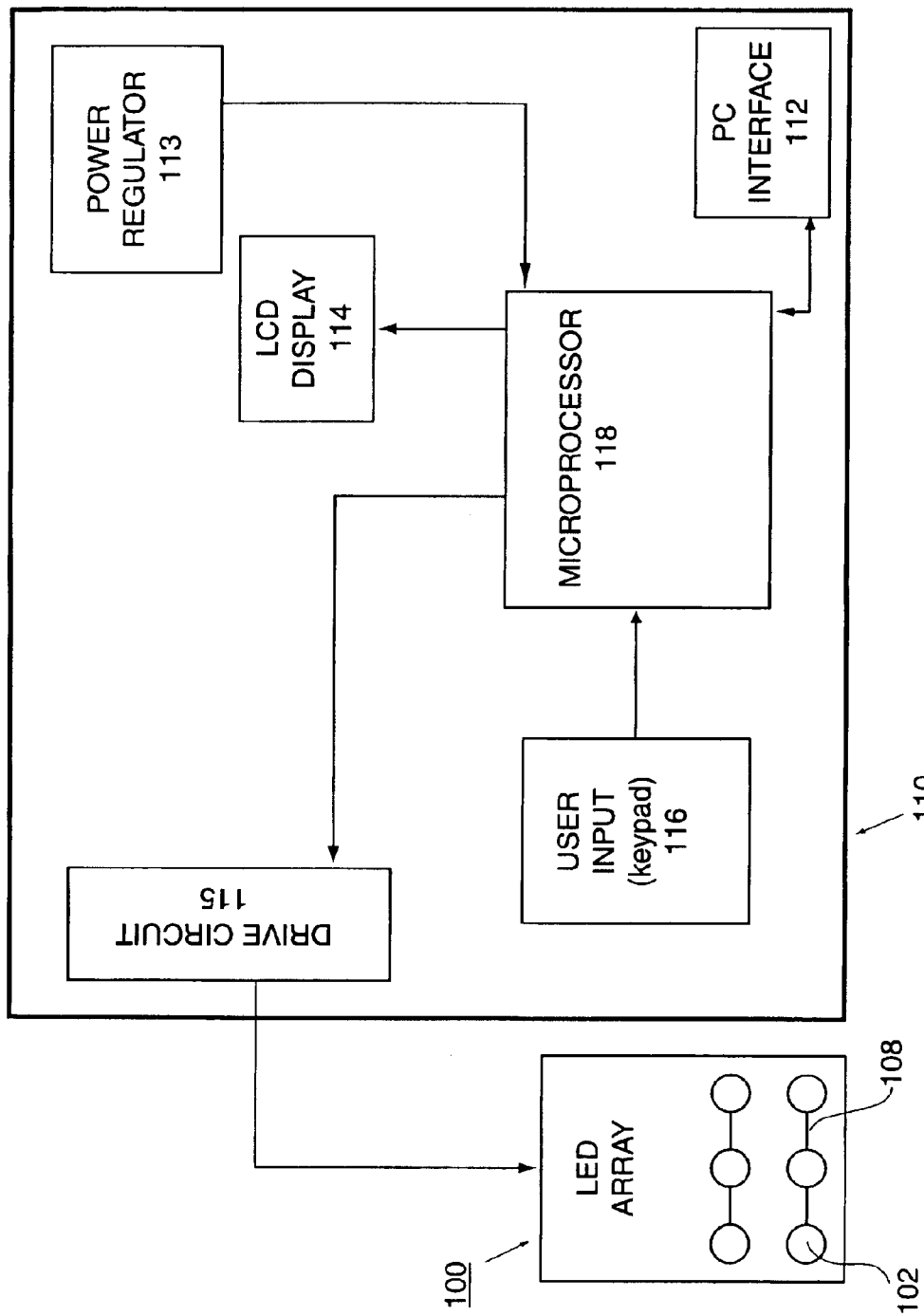
FIG. 3 shows details of a control unit used in this invention.

Details of control unit 110 are shown in the block diagram in FIG. 3, as attached to treatment pad 100. Control unit 110 comprises a user input module 116 such as a keypad, that is used to give instructions to microprocessor 118. Feedback is provided to the user by feedback module 114. Power to microprocessor 118 is regulated by power regulator 113. Microprocessor 118 controls drive circuit 115 which in turn energizes the energy-emitting element array. Optionally, microprocessor 118 communicates directly with a PC via computer interface 112, for example, to download use data from the microprocessor to the PC.

Figure 4:
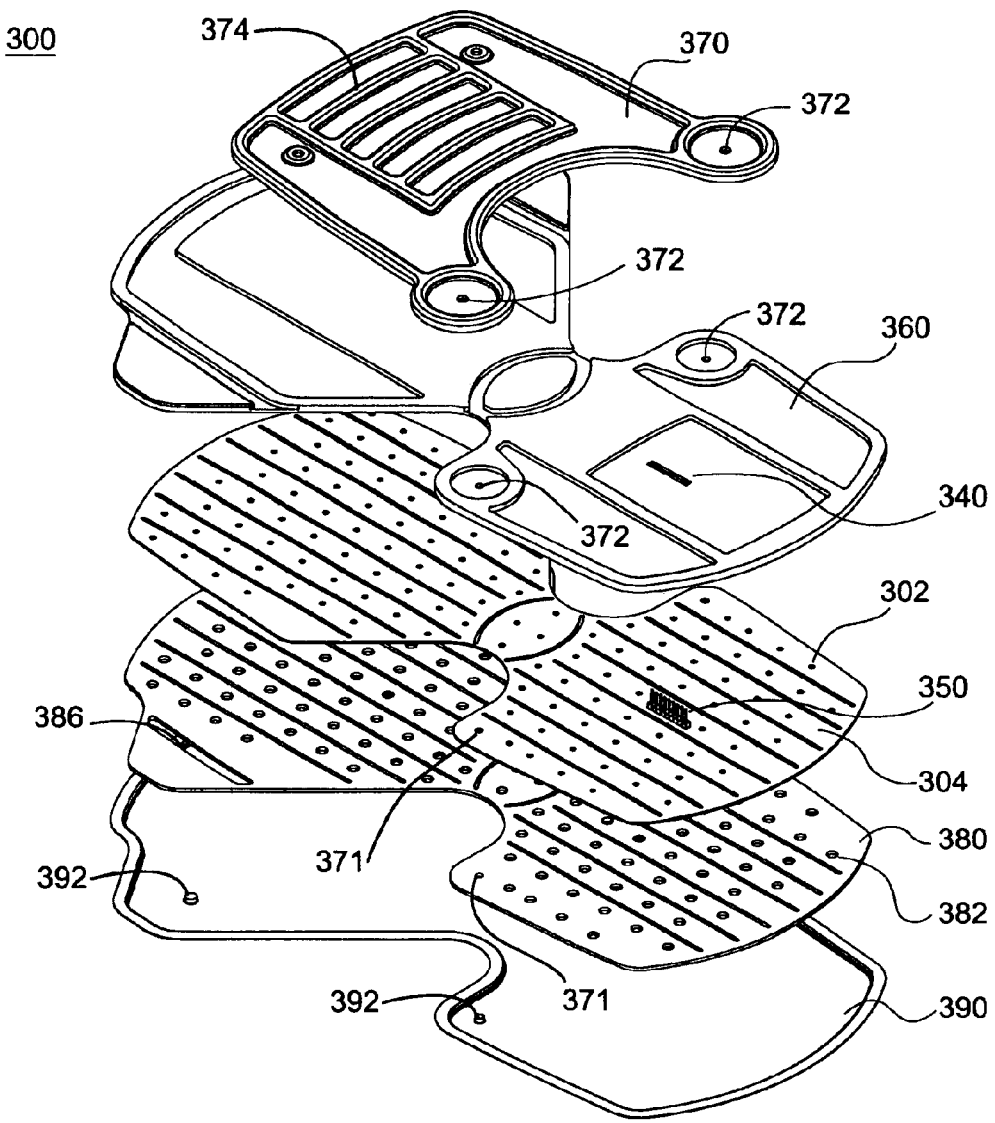
FIG. 4 is an exploded view of one embodiment of the treatment pad of this invention, with optional structural support and protective layers.

An exploded view of one embodiment of the energy-emitting element treatment pad 300 with additional optional structural layers is shown in FIG. 4. In this embodiment, LEDs 302 are arrayed on flexible printed circuit board 304. LEDs 302 are placed such that light is directed downward towards the surface of the treatment pad that is secured or directed towards the patient. Pins 350 provide electrical connection with the control unit or memory module of the device. When the device is fully assembled, pins 350 protrude through slot 340. Optional protective spacing layer 380 has openings 382 aligned with the LEDs such that the protective layer does not impede the light emitted from the LEDs. Protective spacing layer 380 may be sufficiently thick to prevent the LEDs from contacting the patient's skin. Optional protective transparent layer 390 is placed below the energy-emitting element array, or protective spacing layer 380, if present. Protective transparent layer 390 is transparent to light at the wavelength(s) of the LEDs. Optional protective layers shell 360 and stiffener 370 provide additional structural support to the assembly. Optional ridges 374 add additional rigidity to stiffener 370. To assemble this embodiment of the treatment pad, all of the layers present are aligned such that posts 392 pass through alignment holes 371 and snap into attachment holes 372. The fully assembled treatment pad may be applied to an anatomical site by passing an attachment strap (not shown) through slit 386 and securing it around, for example, a limb.

Figure 5:
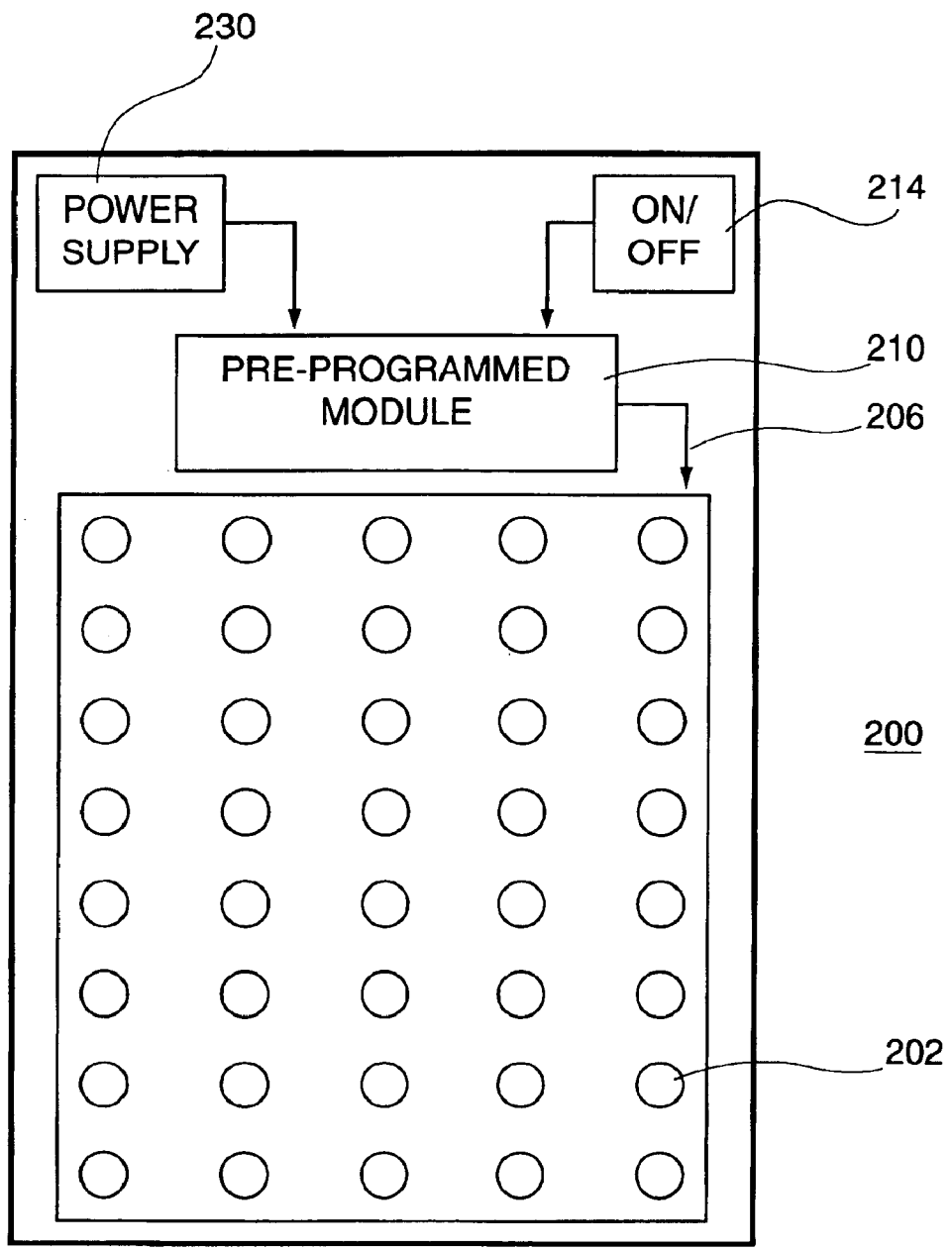
FIG. 5 shows one embodiment of a pre-programmed therapy device of this invention.

FIG. 5 is a block diagram of one embodiment of a pre-programmed device of this invention. In this embodiment, energy-emitting elements 202 are arranged in an array of columns and rows on a substrate to form treatment pad 200. The energy-emitting elements on treatment pad 200 are controlled by a preprogrammed module 210 which is powered by power supply 230. Switch 214 allows the user to turn the unit on and off.

Figure 6:
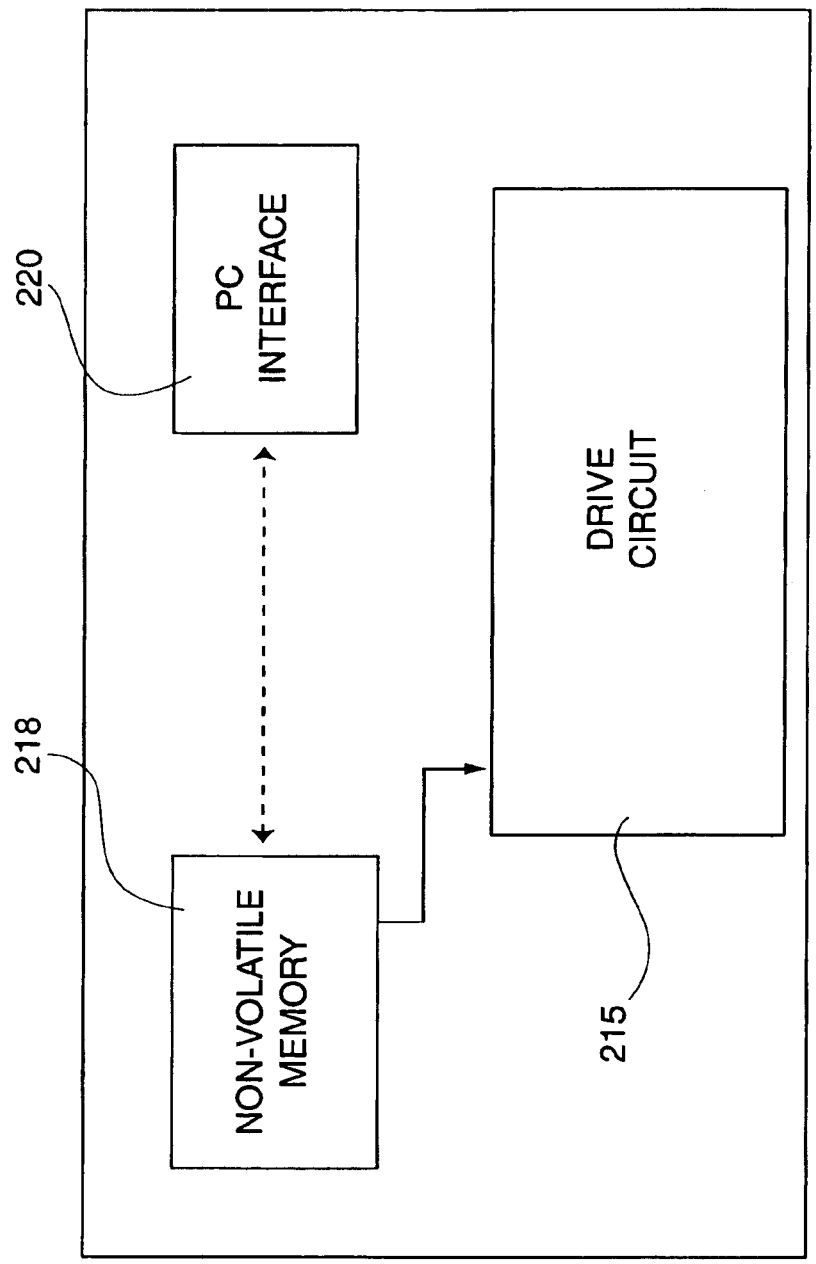
FIG. 6 shows details of one embodiment of a pre-programmed module.

FIG. 6 is a block diagram of details of pre-programmed module 210 which comprises a non-volatile memory module 218 and drive circuit 215. Power is supplied to non-volatile memory module 218, and to the energy-emitting elements 202 (FIG. 5) via power supply 230. Power supply 230 may be a battery, rechargeable battery, or AC adapter. The pre-programmed device may be pre-programmed with one or more programs and the programs may be replaced or modified via optional programmer input 220 (shown in FIG. 6) which may be a PC interface cable such as a USB cable, a smart card, or a simple two-wire cable connected to a microprocessor control unit. The programmer input 220 may also utilize wireless technologies, such as infrared technologies, as are known in the art. Operation of the pre-programmed device is via start button 214. Start button 214 may also be used to select one of several run programs.

Exemplary embodiments of the device of this invention are shown in FIGS. 7–12. FIG. 7A shows one embodiment of how control unit 710 of the device of this invention can be worn by the user. FIG. 7B shows an embodiment of the treatment pad 700 of this invention for use in treating areas of the upper and lower back, or other flat anatomical sites such as the stomach.

FIGS. 8A and 8B show a wrap-around embodiment of treatment pad 800 suitable for application to round anatomical sites such as limbs. The pad may be secured to the limb using any of the methods discussed above including, for example Velcro®. In this embodiment, control unit 810 is attached to treatment pad 800 via cable 806.

FIGS. 9A and 9B show examples of the treatment pad of this invention designed for specific anatomical sites. FIG. 9A depicts an ear and jaw pad 901. FIG. 9B depicts a face and nasal/sinus pad 902. Ear pad 901 is secured to the patient using a flexible earband 903. Nasal/sinus pad 902 is held in place by elastic straps 904.

Figure 10:
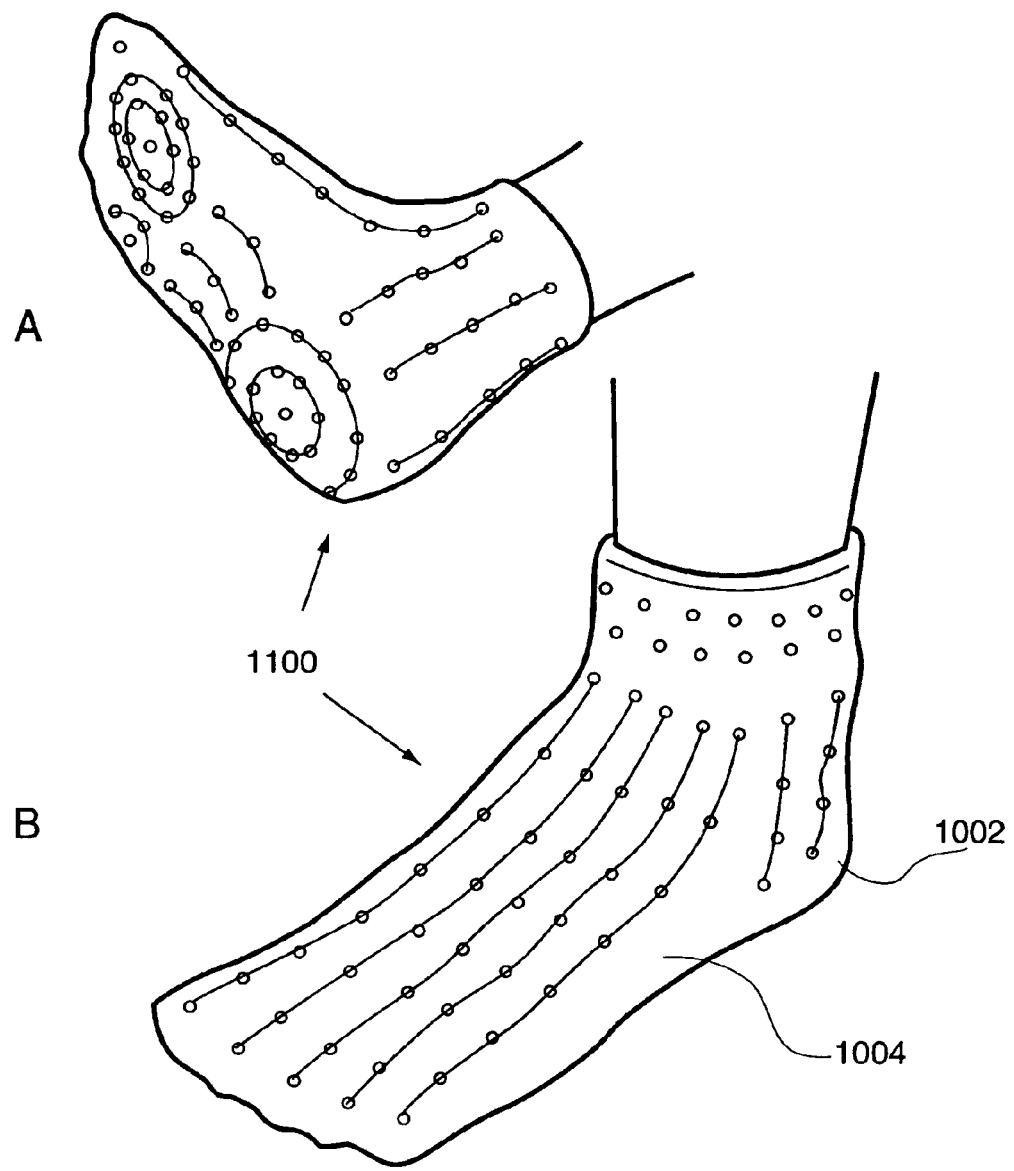
FIG. 10 depicts one example of a 'wearable' embodiment of the device of this invention as applied to the feet.
Figure 11:
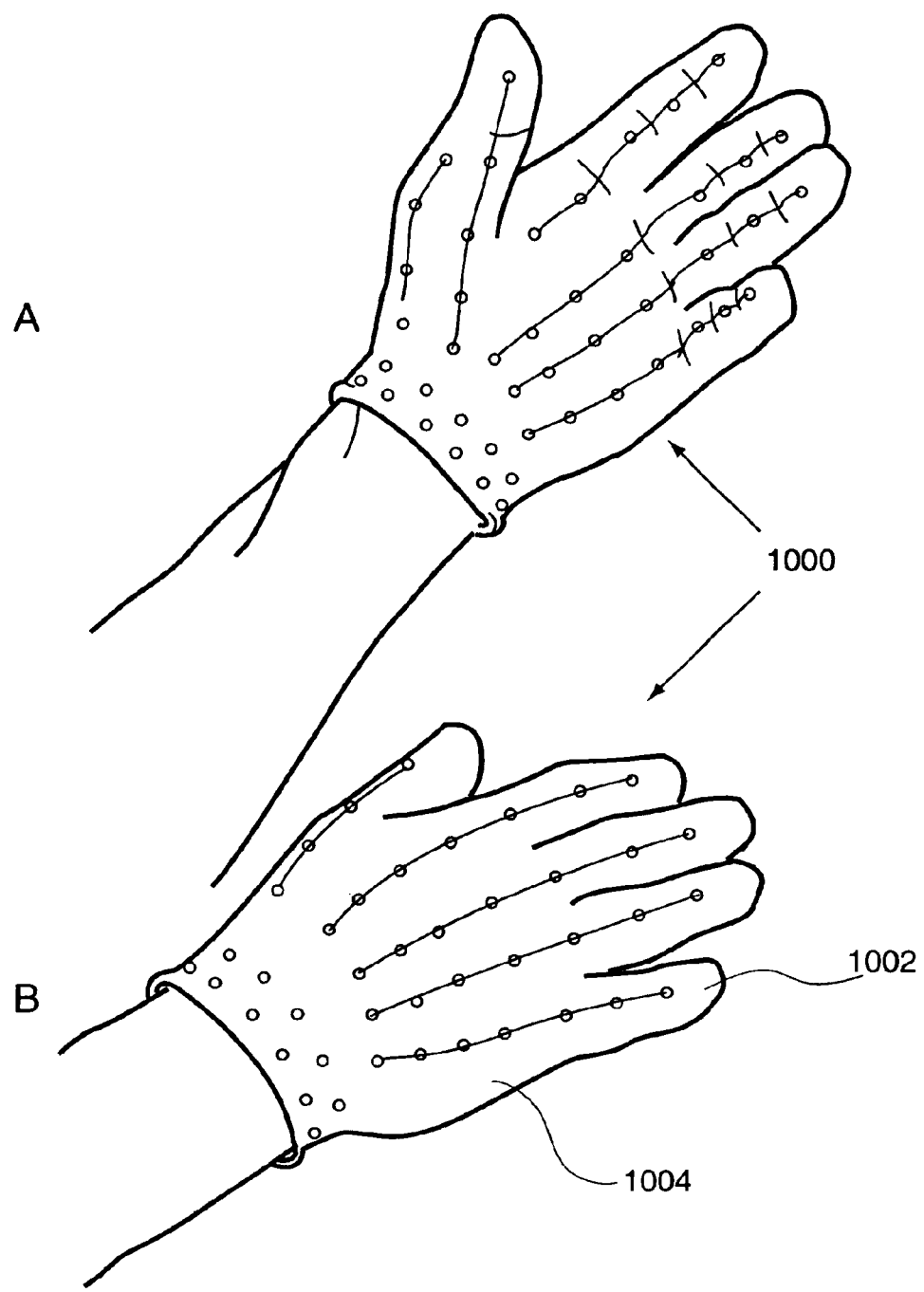
FIG. 11 depicts one example of a 'wearable' embodiment of the device of this invention as applied to the hands.

FIGS. 10 and 11 depict 'wearable' treatment pads 1000 and 1100 for the hands and feet, respectively. In these embodiments, energy-emitting elements 1002 and accompanying circuitry are mounted in a material 1004 that flexes and stretches to fit different sizes and anatomical structures. Suitable materials include but are not limited to cloth, elastic fabric, and elastomeric materials such as rubber and other polymers. Other such wearable designs are readily apparent to one skilled in the art, and include socks, pants, shorts, shirts, hats, and the like.

FIGS. 12A and 12B show one embodiment of the therapy device of this invention designed to be applied to a flexible joint such as a knee or an elbow. In this embodiment, control unit 1210 is mounted directly on treatment pad 1200.

The present invention is not to be limited by the preferred embodiments described herein. Upon reading this specification, those skilled in the art will recognize various modifications thereof. Therefore, it is to be understood that such modifications are intended to fall within the scope of the appended claims and their legal equivalents.

We claim:

1. A method for administering energy therapy to a patient comprising the steps of:
   a) contacting one or more anatomical sites on a patient's body with energy from an energy therapy device, said device comprising:
      (i) a substrate
      (ii) a plurality of groups of energy-emitting elements attached to said substrate;
      (iii) a drive circuit in electrical connection with said energy-emitting elements; and
      (iv) a control unit in electrical connection with said energy-emitting elements; and
   b) programming the control unit to cause the drive circuit to cause the groups of energy-emitting elements to create an energy wave aligned with one or more meridians underlying a contacted anatomical site.

2. The method of claim 1 wherein said step of programming includes programming one or more of wave rate, direction, pulse rate, and treatment time.

3. The method of claim 2 wherein said step of programming comprises programming the wave direction to follow the direction of flow of Qi energy in the one or more acupuncture meridians.

4. The method of claim 2 wherein the wave rate is variable.

5. The method of claim 2 wherein the wave rate varies according to a selected regimen.

6. The method of claim 1 further comprising heating the patient's body, or part thereof, underlying said light therapy device.

7. The method of claim 1 further comprising cooling the patient's body, or part thereof, underlying said light therapy device.

8. The method of claim 1 wherein the energy-emitting elements are chosen from the group consisting of thermal, magnetic, electric, acoustic, pressure, and X-ray emitting elements.

9. The method of claim 1 wherein the energy-emitting elements are light-emitting elements of visible or infrared light.

* * * * *